(12) United States Patent
Chang

(10) Patent No.: US 6,513,929 B2
(45) Date of Patent: Feb. 4, 2003

(54) ERGONOMIC FRAMES FOR TELESCOPIC LOUPES

(76) Inventor: Byung Jin Chang, 5521 Overbrook Dr., Ann Arbor, MI (US) 48105

( * ) Notice: Subject to any disclaimer, the term of this patent is extended or adjusted under 35 U.S.C. 154(b) by 0 days.

(21) Appl. No.: 10/151,379

(22) Filed: May 20, 2002

(65) Prior Publication Data

US 2002/0159024 A1 Oct. 31, 2002

Related U.S. Application Data

(63) Continuation-in-part of application No. 09/802,532, filed on Mar. 7, 2001, now abandoned.

(51) Int. Cl.[7] ............................. G02C 1/00; G02B 25/00
(52) U.S. Cl. ......................................... 351/158; 359/481
(58) Field of Search ................... 351/41, 158; 359/399, 359/407, 409, 481

(56) References Cited

U.S. PATENT DOCUMENTS

| | | | | |
|---|---|---|---|---|
| 3,273,456 A | * | 9/1966 | Feinbloom | 351/158 |
| 3,522,983 A | * | 8/1970 | Daniels | 351/58 |
| 5,428,474 A | * | 6/1995 | Murphy | 351/163 |
| 6,061,189 A | * | 5/2000 | Caplan et al. | 351/158 |

* cited by examiner

Primary Examiner—Huy Mai
(74) Attorney, Agent, or Firm—Gifford, Krass, Groh, Sprinkle, Anderson & Citkowski, PC

(57) ABSTRACT

Ergonomic eyeglass frames are particularly suited to surgical, medical and dental applications. A set of eyeglass frames having a temple portion and lenses arranged in a plane, whereby the angle between the temple portion and the lens plane defines a pantascoptic angle. A pair of surgical telescopes or loupes are mounted through a lower portion of one of the respective eyeglass frames, with the pantascoptic angle preferably being 80 degrees or less to provide a more stable physical mounting of the telescope or loupe through the lower portion of each lens element.

1 Claim, 1 Drawing Sheet

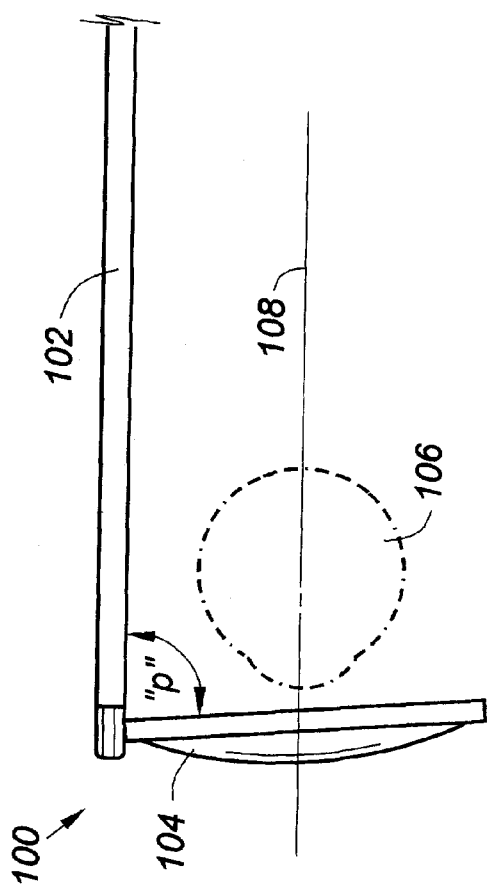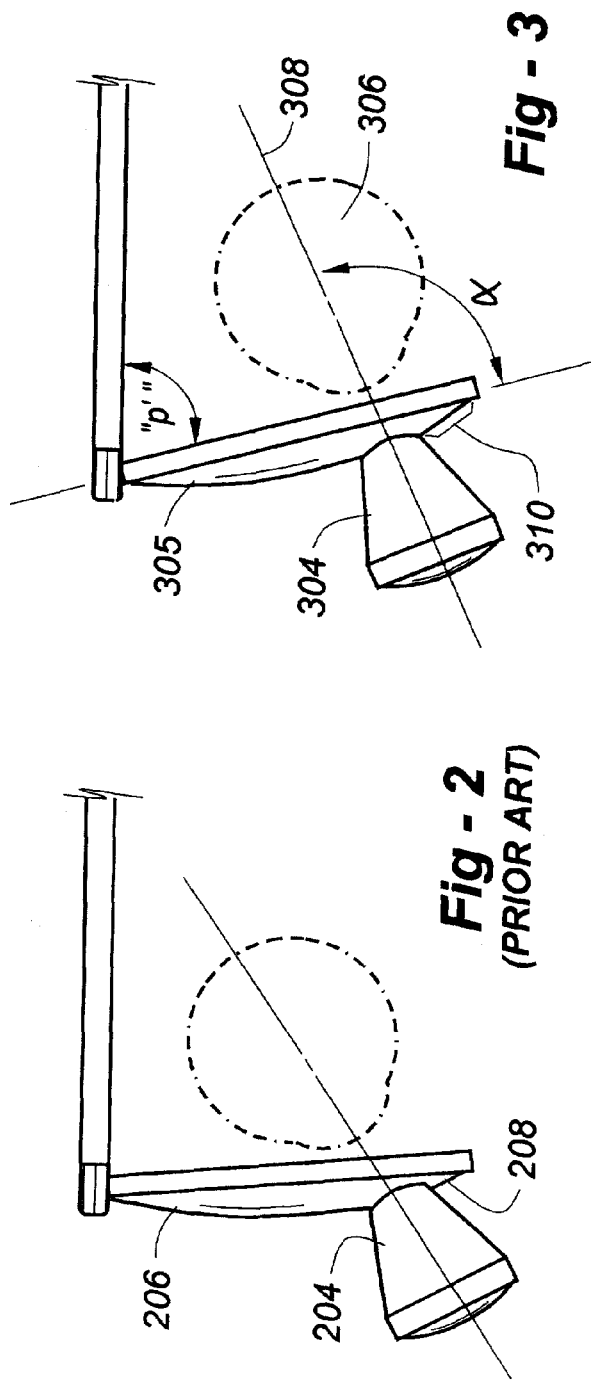

ERGONOMIC FRAMES FOR TELESCOPIC LOUPES

REFERENCE TO RELATED APPLICATION

This application is a continuation-in-part of U.S. patent application Ser. No. 09/802,532, filed Mar. 7, 2001 now abandoned. The content of this application is incorporated herein by reference.

FIELD OF THE INVENTION

This invention relates generally to magnification eyewear and, in particular to improved eyeglass frames particularly for physicians, surgeons and other medical professionals.

BACKGROUND OF THE INVENTION

Many clinical procedures require a large declination angle, which is defined as the angle that a person's eyes makes to the horizon when looking down. Accommodating a large declination angle in conjunction with through-the-lens surgical telescopes is often very limited due to the physical constraints of the eyeglasses. In particular, the typical pantascoptic angle, which is defined as the angle between the temple and the plane of the lenses, is generally at or near 90 degrees, which makes the mounting of through-the-lens loupes at a high declination angle problematic.

This situation is depicted in FIGS. 1 and 2. FIG. 1 depicts schematically a pair of eyeglasses at 100, wherein a pantascoptic angle "p" is defined between a temple portion 102 and the plane of the lenses 104 as shown. The eyeball is shown at 106, which lies on an optical axis 108. As is typical, the angle "p" is very close to 90 degrees, often on the order of 80 degrees or more.

As shown in FIG. 2, when surgical telescopes 204 are physically bonded through a lower section of the glass or plastic comprising the lenses, this near 90 degree pantascoptic angle creates significant problems, often resulting in physical instability. In particular, when surgical telescope 204 is mounted/cemented through the lower portion of the lens 206 at a relatively large declination angle little, or no area 208 remains between the mounting and the bottom of the lens. This results in a narrow band of lens material which is very fragile, such that if the slightest force is received on the upper portion of the telescope 204, breakage or dislodging of the assembly may occur.

SUMMARY OF THE INVENTION

This invention improves on the prior art by providing ergonomic eyeglass frames particularly suited to surgical, medical and dental applications. The invention includes a set of eyeglass frames having a temple portion and lenses arranged in a plane, whereby the angle between the temple portion and the lens plane defines a pantascoptic angle. A pair of surgical telescopes or loupes are mounted through a lower portion of one of the respective eyeglass frames, and the pantascoptic angle is preferably 80 degrees or less to provide a more stable physical mounting of the telescope or loupe through the lower portion of each lens element.

BRIEF DESCRIPTION OF THE DRAWINGS

FIG. 1 is a drawing of a prior art pair of eyeglass frames featuring a near-90-degree pantascoptic angle;

FIG. 2 is a drawing of a prior art through-the-lens loupe arrangement showing the mounting problem that results from a near-90-degree pantascoptic angle and large declination angle; and FIG. 3 is a drawing of a through-the-lens loupe arrangement according to the invention, showing the mounting problem is relieved with a greater than 90-degree pantascoptic angle and large declination angle.

DETAILED DESCRIPTION OF THE INVENTION

This invention solves the problem of mounting a surgical telescope through eyeglasses by decreasing the pantascoptic angle between the temple portion and lens plane of the eyeglass frames, thereby providing a more stable region for the mounting of though-the-lens type telescopes or loupes.

A preferred embodiment is shown in FIG. 3, wherein, with the eyeball 306 of the practitioner looking downwardly through the loupe 304 along axis 308, much more area 310 remains at the bottom portion of the lens, thereby affording a much more stable mounting assembly.

In the preferred embodiment, the eyeglass frames 300 according to the invention are provided having a pantascoptic angle Of preferably less than 90 degrees such that the plane of the eyeglass lenses is transversed to the optical axis 306 when the practitioner is looking through the loupe or telescope 304. In such situations, the angle may be on the order of 60–80 degrees, or thereabouts. Not only does this arrangement provide for a more stable mounting of the loupe 304, through the use of a reduced pantascoptic angle, the angle a between the axis 308 of the loupe 304 and the plane of the lenses 305 may be made substantially 90 degrees, thereby bringing the loupe 304 much closer to the eyes of the practitioner, increasing field size and reducing aberration.

I claim:

1. Ergonomic eyeglass frames particularly suited to surgical, medical and dental applications, comprising:
    a set of eyeglass frames having a temple portion and lenses arranged in a plane, whereby the angle between the temple portion and the lens plane defines a pantascoptic angle;
    a pair of surgical telescopes or loupes, each having an optical axis and being supported by one of the respective eyeglass lenses; and
    wherein the pantascoptic angle is less than 80 degrees and the angle formed by the optical axes of the telescopes or loupes and the plane of the lenses is substantially 90 degrees.

* * * * *